United States Patent [19]

Whitaker

[11] 4,205,057

[45] May 27, 1980

[54] CEREBROSPINAL FLUID PROTEIN FRAGMENTS

[75] Inventor: John N. Whitaker, Memphis, Tenn.

[73] Assignee: Government of the United States, Washington, D.C.

[21] Appl. No.: 870,090

[22] Filed: Jan. 17, 1978

[51] Int. Cl.² .................... G01N 33/16; A61K 43/00
[52] U.S. Cl. ........................................ 424/1; 424/12; 23/230 B
[58] Field of Search ................. 424/1, 12; 23/230 B

[56] References Cited
PUBLICATIONS

Fritz et al., Fed. Proc., vol. 36, No. 3, Mar. 1, 1977, p. 1297.

*Primary Examiner*—Benjamin R. Padgett
*Assistant Examiner*—Christine M. Nucker
*Attorney, Agent, or Firm*—Holman & Stern

[57] ABSTRACT

The isolation and use of cerebrospinal fluid myelin encephalitogenic protein (EP) fragments as an indicator of disease activity in multiple sclerosis is disclosed. With the use of a double-antibody radioimmunoassay, it was determined that a portion of EP cross-reacting with residues 43-88 (EP-Pl) appears in the cerebrospinal fluid during periods of exacerbation.

3 Claims, No Drawings

CEREBROSPINAL FLUID PROTEIN FRAGMENTS

BACKGROUND AND SUMMARY OF THE INVENTION

The present invention relates to the isolation and use of cerebrospinal fluid myelin encephalitogenic protein fragments as an indicator of disease activity in multiple sclerosis.

Central nervous system (CNS) myelin is known to be composed of 70 percent lipid and 30 percent protein. The major protein components are proteolipid, a basic or encephalitogenic protein (EP), and an acidic protein (s) termed Wolfgram protein. EP appears to be a structural element of the myelin sheath and has been extensively investigated because it can induce experimental allergic encephalomyelitis in a variety of laboratory animals. EP comprises 30 percent of CNS myelin proteins, has a molecular weight of 18,500 daltons, and contains 169 amino acid residues, the sequence of which is known for the bovine and human proteins.

The biosynthesis and degradation of EP have not been elucidated. EP is diminished in the CNS lesions of multiple sclerosis, but the mechanisms involved in removal of EP in such areas are uncertain. Degradation of EP may involve brain acid proteinase, a cathepsin D-like endopeptidase, which cleaves EP at selected sites in a limited manner to produce fragments containing residues 1-42, 43-88, and 89-169, as described, for example, by N. Marks et al., *Biochem. Biophys. Res. Commun.*, 56: 68–74 (1974) and by M. Benuck et al., *Eur. J. Biochem.*, 52: 615–621 (1975). Brain acid proteinase has been found to be increased in both experimental allergic encephalomyelitis and in the lesions of multiple sclerosis. Different fragments generated by acid proteinase activity differ in encephalitogenic and antigenic activities, as described by E. R. Einstein et al., *Immunochemistry*, 9: 73–84 (1972).

In accordance with the present invention, a determination has been made that cerebrospinal fluid (CSF) from multiple sclerosis patients contains EP or fragments thereof which are of diagnostic aid and serve as an index of disease activity. With the use of a double-antibody radioimmunoassay, it has been demonstrated that a portion(s) of EP cross-reacting with residues 43-88 (EP-P1) appears in the CSF during periods of exacerbation. It is noted here that the number of amino acid residues is based on that of bovine EP. P1 is the first fraction eluted during ion exchange chromatography of pepsin-generated EP fragments, as discussed by F. Chou et al., *J. Biol. Chem.*, 251: 2671–2679 (1976).

DESCRIPTION OF THE PREFERRED EMBODIMENTS

In carrying out the present invention, brain and cerebrospinal fluid samples were obtained as follows:

Postmortem cerebral tissue was obtained within 4 hours of death from two persons. Patient A was an 84-year-old man with bronchogenic carcinoma who had no antemortem neurologic deficit and whose brain showed no lesions on the surface or on sectioning. Patient B was a 52-year-old man with a 12-year history of multiple sclerosis. The brain and spinal cord of patient B had widespread, multiple lesions that on microscopic examination had the appearance of chronic multiple sclerosis plaques. Brain tissue was frozen and stored at −60° C. until processed.

CSF was obtained at the time of diagnostic lumbar puncture from 43 patients with multiple sclerosis in various disease phases, from 108 with other neurologic disorders and from nine with non-neurologic disorders. With the exception of one patient who was in an initial attack, all 43 patients classified as having multiple sclerosis had experienced two or more episodes of CNS impairment or otherwise fulfilled the criteria for probable (clinically definite) multiple sclerosis. Persons with idiopathic chronic (eight patients) or acute transverse (one patient) myelopathy were categorized separately. CSF was stored at −20° C. See Tables I and II.

Preparation of EP and EP-P1

From each brain specimen a pH 3 extract was obtained in accordance with the method as set forth by G. E. Deibler et al., *Prep. Biochem.*, 2: 139–165 (1972), incorporated herein by reference. This extract was chromatographed separately on CM-cellulose. The last fraction, termed fraction 6, eluting with a NaCl gradient was pooled, desalted on Sephadex G-25 coarse in 0.5 percent acetic acid, and lyophilized. The general procedure for preparation of such fractions is set forth by F. Chou et al., *J. Biol. Chem.*, 251: 2671–2679 (1976), incorporated herein by reference. EP fraction 6 of patient B was used without further purification for preparation of the immunogen. To remove more cathodally migrating materials, presumably degradation products of EP from the EP preparation used in the radioimmunoassay, EP fraction 6 of patient A was subjected to gel filtration on a 1.5 by 90 cm column of Sephadex G-100 equilibrated with 0.2 M ammonium bicarbonate and monitored at an absorbance of 225 nm. The major peak eluting at 45 percent of the gel bed volume was lyophilized twice and used for radiolabeling and in the radioimmunoassay as unlabeled inhibitor standard.

Table I

| Control group of 117 persons with conditions other than multiple sclerosis | |
|---|---|
| Condition | Number |
| Subacute sclerosing panencephalitis | 4 |
| CNS infection | 8 |
| Encephalitis (6)* | |
| Trigeminal herpes zoster (1) | |
| Cryptoccal meningitis (1) | |
| Optic atrophy | 3 |
| Spinocerebellar degeneration | 6 |
| Neoplastic disease | 10 |
| Multiple myeloma (2) | |
| Hematologic malignancy with neurologic involvement (6) | |
| Intracranial primary tumor (2) | |
| Cervical cord trauma (2 weeks to 4 months prior) | 5 |
| Myelopathy | 9 |
| Chronic (8) | |
| Acute (1) | |
| Motor neuron diseases | 6 |
| Chronic peripheral neuropathy | 6 |
| Guillain-Barre syndrome | 4 |
| Miscellaneous | 56 |
| Cerebrovascular diseases (7), myasthenia gravis (2), neurosyphilis (1), pernicious anemia (1), systemic lupus erythematosus with (1) and without (1) CNS manifestations, radiation myelopathy (1) and syringobulbia (1) | |

*Numbers in parentheses indicate number of individuals in the subgroups.

Table II

Clinical data and cerebrospinal fluid findings in 14 patients with multiple sclerosis in acute phases of disease

| Number | Age, race sex | Duration of disease (years) | Time since onset of exacerbation (days) | Cerebrospinal fluid Protein (mg/100 ml) | IgG (%) | Cells (per mm$^3$) RBC | WBC | Cells (% of WBC) PMN | Mono | EP-P1 ng/ml |
|---|---|---|---|---|---|---|---|---|---|---|
| 1 | 31 WF | 8 | 2 | 96 | 18 | 0 | 28 | 40 | 60 | 15.4 |
| 2 | 52 BF | 7 | 3 | 96 | 18 | 315 | 43 | 24 | 76 | 10.2 |
| 3 | 28 WM | 8 | 6 | 81 | 11 | 11 | 2 | 0 | 100 | 4.4 |
| 4 | 18 BF | 0.4 | 5 | 44 | 23 | 0 | 49 | 1 | 100 | 6.4 |
| 5 | 17 BF | 1 | 10 | 40 | 38 | 0 | 7 | 0 | 100 | 3.4 |
| 6 | 7 BF | 0.2 | 1 | 69 | 16 | 0 | 32 | 19 | 81 | 7.4 |
| 7 | 33 WM | 2 | 1 | 55 | 14 | 0 | 4 | 0 | 100 | 12.8 |
| 8 | 36 WM | 6 | 14 | 57 | 18 | 0 | 7 | 15 | 85 | 4.8 |
| 9 | 26 WM | 2 | 2 | 61 | 17 | 675 | 0 | 0 | 0 | 0 |
| 10 | 26 WM | 8 | 8 | 48 | 31 | 322 | 2 | 0 | 100 | 0 |
| 11 | 28 WM | 1.5 | 8 | 50 | 12 | 0 | 1 | 0 | 100 | 0 |
| 12 | 29 BM | 1.5 | 9 | 51 | 10 | 0 | 52 | 0 | 100 | 0 |
| 13 | 21 WF | 2 | 10 | 57 | 25 | 44 | 14 | 20 | 80 | 0 |
| 14 | 23 WM | 2.3 | 8 | 96 | 19 | 60 | 45 | 4 | 96 | 0 |

The acid extract from patient A was also chromatographed on CM-cellulose and processed in an identical manner, except that fractions 3–6 were collected with a stepwise NaCl gradient and pooled, desalted, and lyophilized. Since the extent of phosphorylation, deamidization, and loss of C-terminal arginine residues that account for bovine EP microheterogeneity does not involve residues 43–88, fractions 3–6 were pooled to provide more starting material to prepare EP-P1. This material was exposed to pepsin to produce EP-P1, employing the procedure of E. H. Eylar et al., *J. Biol. Chem.*, 246: 3418–3424 (1971), incorporated herein by reference. 100 mg of EP and 0.5 mg of pepsin were dissolved in 21 ml 0.05 M ammonium acetate, pH 3.5 and shaken at 37° C. in a water bath for 90 minutes. This material was lyophilized, dissolved in 20 ml 0.02 M ammonium bicarbonate, pH 7.5 and chromatographed at 25° C. on a 2.6 by 15 cm column of CM-cellulose at pH 7.5. The sharp peak eluting at 6 to 7 mMHOs of conductivity (approximately 0.12 M NaCl) was lyophilized, desalted on Bio-Gel P-2 in 0.5 percent acetic acid, and relyophilized.

Preparation of antisera

Fraction 6 of the EP from patient B was conjugated with RSA and used to immunize rabbits, following the method of J. N. Whitaker et al., *J. Biol. Chem.*, 250: 9106–9111 (1975), incorporated herein by reference. Serum (R79-P86-BIII8) obtained from one rabbit 12 weeks after beginning immunization with multiple sclerosis EP was used for the radioimmunoassay. This antiserum was selected because initial studies of a number of antisera to EP demonstrated that it had an unusually high degree of reactivity with human EP-P1 and permitted a greater sensitivity in the assay system.

Human IgG was isolated by DEAE-cellulose chromatography, following the method of J. R. Mendell et al., *J. Immunol.*, 111: 847–856 (1973), incorporated herein by reference. A New Zealand white female rabbit was injected with an inoculum (1.5 ml) containing 325 μg of human IgG in complete Freund's adjuvant. A second injection of 300 μg of human IgG in incomplete Freund's adjuvant was administered after 14 days, and blood was obtained 10 days later. By immunoelectrophoresis, the isolated IgG was free of other human serum proteins, and the rabbit antihuman IgG reacted only with IgG in normal human serum. Goat antirabbit IgG was prepared as previously described, following the method of J. N. Whitaker, *J. Immunol.*, 114: 823–828 (1975), incorporated herein by reference.

Radiolabeling

Human EP fraction 6, after Sephadex G-100 gel filtration, from patient A was radioiodinated by the chloramine T method, in accordance with the procedure set forth by G. Schmid et al., *Eur. Neurol.*, 12: 173–185 (1974), incorporated herein by reference. A 0.7 by 13 mm Bio-Gel P-2 column equilibrated with 0.01 M HCl containing 1 gm of BSA per 100 ml was used to separate bound from unbound $^{125}$I. A single tube in the initial peak (25 percent gel bed volume) containing the maximum number of cpm was used. Five percent trichloroacetic acid precipitated 95 to 98 percent of the cpm added.

EP-P1 was radioiodinated with carrier-free $^{125}$I by the lactoperoxidase method, following the method set forth by D. R. Phillips, et al., *Biochemistry*, 10: 1766–1771 (1971), incorporated herein by reference. Lactoperoxidase-catalyzed iodination was more consistent than the chloramine T procedure in producing radiolabeled EP-P1 with satisfactory specific activity. Radiolabeled antigen was separated from free iodine on a P-2 column as previously described for $^{125}$I-EP. At a concentration of 5 percent trichloroacetic acid, 10 to 20 percent of the cpm were precipitable. This low percentage of precipitability may be due in part to the size of the polypeptide. Since only 85 percent of the $^{125}$I human EP-P1 could be precipitated with low dilutions of certain anti-EP antisera, radioiodination-induced changes of EP-P1 must also be considered.

Radioimmunoassays

Double-antibody radioimmunoassays were performed in a total volume of 0.95 ml in 12 by 75 mm polypropylene plastic tubes. The assay mixture consisted of 0.2 M TRIS-acetate buffer, pH 7.2, containing 0.2 gm methylated BSA (TA-MBSA) per 100 ml, 0.2 ml of rabbit anti-EP appropriately diluted in the TRIS-acetate buffer containing a 1:200 dilution of normal rabbit serum, standard or test CSF in 50 μl, and 17,000 to 20,000 cpm of $^{125}$I-EP or $^{125}$I-EP-P1 in 50 μl of the TRIS-acetate buffer. The replacement of BSA with MBSA was required to reduce the precipitation of radiolabeled antigen by buffer or nonimmune serum to below 5 percent. This amount of cpm necessitated adding approximately 900 pg of $^{125}$I-EP or 300 pg of $^{125}$I-EP-P1 to each tube (vide infra). Preliminary studies revealed that with $^{125}$I-EP a delay of 1 day between addition of unlabeled EP and $^{125}$I-EP increased the amount of inhibition caused by the unlabeled EP. With $^{125}$I-EP-P1, the inhibition by unlabeled EP-P1 was not enhanced by a similar delay. Hence, in assays using $^{125}$I-EP but not $^{125}$I-EP-P1, the radiolabeled antigen was added after the mixture of unlabeled EP or CSF to be tested, buffer, and diluted anti-EP had stood at 4° C. for 20 hours. The unlabeled EP or EP-P1 and thymic histone were stored at −20° C. at a concentration of 10 μg per milliliter in the working buffer used for quantitative complement fixation and diluted to the desired extent in TA-MBSA prior to radioimmunoassay. Twenty hours after addition of radiolabeled antigen, 0.2 ml of goat antirabbit IgG was added, and the mixture was allowed to stand for 24 hours at 4° C. The tubes were centrifuged, the pellet washed with 2 ml of the TRIS-acetate buffer, and the radioactivity of the pellet determined on an autogamma counter. All determinations were done in triplicate. For the standard curve, outliers in the triplicate values were rejected.

Other methods

Electrophoresis was performed in 10 percent polyacrylamide gels in TRIS-glycine buffer at pH 8.8. Samples were subjected to electrophoresis of 1 mA per gel for 2.5 hours at 20° C. toward the cathode. Electrophoresis was also conducted on 0.6 by 65 mm 5 percent acrylamide gels containing 8 M urea at pH 2.5 in 1 M acetic acid. Electrophoresis was performed toward the cathode for 75 minutes at 20° C. with 2.5 mA per gel. Gels were stained in amidoschwarz and destained in 3 percent acetic acid. Amino acid analysis of EP-P1 was performed on a Beckman 120C Analyzer on hydrolyzates prepared in constant-boiling HCl at 108° C. for 24 hours in tubes sealed under nitrogen. For more accurate measurement of the valine content of EP-P1, acid hydrolysis was extended to 72 hours. CSF total protein was determined by the Folin-phenol method with a standard of crystalline BSA. CSF IgG concentrations were determined using human IgG standards and rabbit antihuman IgG prepared as previously described. The relationships among CSF total protein, percentage of IgG and EP-P1 were evaluated by linear regression analysis.

In one study, electrophoresis was carried out in 10 percent polyacrylamide gels at pH 8.8 of (1) EP fraction 3-6, (2) EP fraction 6 from patient B, (3) pepsin digest of EP fraction 3-6, (4) EP-P1 isolated by CM-cellulose chromatography, and (5) EP fraction 25 μg per gel. Electrophoresis and photography of gel 5 were performed on a different occasion from that of gels 1-4. (Cathode at bottom).

In another study, electrophoresis was carried out in 5 percent polyacrylamide gels at pH 2.5 in 8 M urea of (1) EP fraction 3-6, (2) pepsin digest of EP fraction 3-6, (3) EP-P1 isolated by CM-cellulose chromatography, (4) EP fraction 6 from patient B, and (5) EP fraction 6 from patient A following Sephadex G-100 gel filtration; 25 μg of protein per gel. (Cathode at bottom).

Characterization of EP and EP-P1

On electrophoresis at pH 8.8 EP, both fraction 6 and fractions 3-6 showed one major band and several minor bands that migrated further toward the cathode. These minor bands are presumably breakdown products of EP. At pH 2.5 in 8 M urea, the multiplicity of bands was more evident. The EP fraction 6 used in the radioimmunoassay was subjected to gel filtration over Sephadex G-100, after which only one band was noted at pH 8.8. At pH 2.5, trace material with slightly greater cathodal migration was still present, as was a more anodal doublet band, probably a polymer of EP.

Electrophoresis of EP following treatment with pepsin revealed one major band and several minor bands at pH 8.8 with no band in the expected position of intact EP.

In a third study, chromatography of pepsin digest of human EP was carried out on CM-cellulose equilibrated with 0.02 M ammonium bicarbonate, pH 7.5. The attached EP fragments were eluted with a 0 to 0.3 M NaCl linear gradient in the same buffer. The peak eluting at 6 to 7 mMHOs was pooled and used as EP-P1. One major peak and several smaller and less-defined peaks were separated by ion exchange chromatography on CM-cellulose. The major fraction eluting at 6–7 mMHOs was designated as EP-P1 based on the behavior of bovine EP fragments under these chromatographic conditions.

EP-P1 migrated as one heavy band at pH 8.8 at a position closer to the anode than EP. A similar position of migration of bovine EP-P1 in this electrophoretic system has been reported in *Eur. J. Biochem.*, 52: 615–621, 1975. The other fragments of EP generated by treatment with pepsin had been removed by the CM-cellulose chromatography at pH 7.5. At pH 2.5, EP-P1 appeared as two bands migrating close to the cathode. The amino acid composition of EP-P1, identified as residues 43-88 agreed well with the expected composition of this portion of the EP molecule. (See Table III). The nature of the second band at pH 2.5 has not been clarified but is probably a fragment consisting of residues 37-88, which is also produced by pepsin treatment of EP and coelutes with residues 43-88 in the CM-cellulose chromatographic system used. The EP fragment used will be referred to as EP-P1 even though it is composed of at least two different peptides.

Radiolabeling of antigen

EP and EP-P1 adhere to gel filtration media; this tendency to adhere was reduced by using 0.01 N HCl containing 1 gm of BSA per 100 ml, but an appreciable amount of radioiodinated material continued to stick to the media. This stickiness necessitated further studies for calculations of specific activity. When a portion of the fraction of radiolabeled antigen was refiltered over Bio-Gel P-2, 20 to 32 percent eluted in the position of the peak fraction, and approximately 80 percent of the total cpm added could be eluted. Based on the recovery in the peak tube, specific activity was calculated to be 20 μCi per microgram for EP and 40 μCi per microgram for EP-P1. This indicated that 300 pg of $^{125}$I-EP-P1 or 900 pg of $^{125}$I-EP was added to each assay tube.

Table III

| Amino acid analysis of human encephalitogenic protein fragment P1 | | |
|---|---|---|
| Amino acid | Calculated | Expected |
| Aspartic acid | 3.9 | 4*+ |
| Threonine | 1.9 | 2 |
| Serine | 4.1 | 4+ |
| Glutamic acid | 3.1 | 3 |
| Proline | 4.0 | 4 |

Table III-continued
Amino acid analysis of human encephalitogenic protein fragment P1

| Amino acid | Calculated | Expected |
|---|---|---|
| Glycine | 7.4 | 7+ |
| Alanine | 3.3 | 3 |
| Half cystine | 0 | 0 |
| Valine | 1.2++ | 2 |
| Methionine | 0.2 | 0 |
| Isoleucine | 0.4 | 0+ |
| Leucine | 1.1 | 1+ |
| Tyrosine | 0.9 | 1 |
| Phenylalanine | 2.4 | 2+ |
| Lysine | 3.4 | 3 |
| Histidine | 4.6 | 5 |
| Arginine | 4.0 | 4+ |

*Number of residues in fragment 43-88 of human EP.
+The additional presence of fragment 37-88 in EP-P1 would contribute to these amino acids.
++Value for 72-hour acid hydrolysis was 1.9.

Reactivity of anti-EP with EP and EP-P1.

The reactivity of anti-EP with $^{125}$I-EP was much greater than with $^{125}$I-EP-P1, typically a difference of approximately 15-fold. A dilution providing approximated 50 percent precipitation of radiolabeled antigen was used in radioimmunoassays to assess reaction by inhibition. With a mixture of anti-EP diluted 1:14,000 and $^{125}$I-EP, inhibition by EP occurred to a level of 1 ng per assay tube with 70 percent inhibition by 100 ng. On the contrary, if EP-P1 was used as inhibitor, virtually no inhibition was effected by 100 ng of this fragment. This result agrees with previous complement-fixation studies reported in J. Biol. Chem., 250: 9106-9111 (1975), incorporated herein by reference, indicating that EP-P1 poorly inhibits the reaction between EP and anti-EP raised by the described method. However, if EP-P1 was radiolabeled, there was inhibition by EP-P1 and, to a slightly lesser extent, EP. For this reaction, anti-EP had to be used at a lower dilution.

Radioimmunoassay for CSF EP fragments

In studies using $^{125}$I-EP and unconcentrated CSF from multiple sclerosis and control patients, there was no inhibition by any of the CSFs. This negative result suggested that EP did not occur in CSF; it occurred in very low levels (below the detectable range of 20 ng per milliliter), or it existed as fragments that could not be effectively detected. After EP-P1 was found in CSF (see below), CSFs were reexamined for EP to be certain that CSFs with EP-P1 had been analyzed. Eleven persons showing CSF EP-P1 levels of 0 to 15.4 ng per milliliter had no detectable EP in this radioimmunoassay system.

Since the use of $^{125}$I-EP-P1 led to the ready detection of EP-P1 and increased the assay sensitivity for EP, CSF was examined in the radioimmunoassay system with EP-P1 as radiolabeled antigen. The identity of the CSF material measured by interference in the radioimmunoassay reaction between anti-EP and $^{125}$I-EP-P1 is unclear. It may be only a portion of EP-P1 or involve much, if not all, of the EP molecule extending beyond residues 43-88. Because EP-P1 was employed as the assay standard and because of the comparative inhibitory effects, the material detected will be referred to as EP-P1. Validation studies of the radioimmunoassay with $^{125}$I-EP-P1 were performed according to recommendations. The range of detection was 100 to 5,000 pg of EP-P1 per assay tube. The lowest level for reproducible detection was 100 pg per assay tube. In the radioimmunoassay, 50 μl of CSF was added per assay tube so that the lower limit of detection was 2 ng per milliliter of CSF. Within-assay variability was ±3 percent. Between-assay variability of CSF was ±10 percent, and within this variation, thawing and refreezing CSF specimens at least four times did not affect the results. A one-to-one dilution of CSF containing EP-P1 resulted in a 50 percent reduction in the measured level of EP-P1. Recovery of EP-P1 added to normal CSF at levels of 0.5 and 1.0 ng per assay tube was 80 to 110 percent. As much as 1,000 ng per assay tube of thymic histone failed to produce any inhibition in this radioimmunoassay.

Of the 43 persons with multiple sclerosis, 14 had recently had an acute episode (Table II); the other 29 were stable or showed a progressive course. Eight of 14 acute patients showed a concentration of EP-P1 in the CSF of greater than 2 ng per milliliter, the least detectable level. Of seven patients who were within 7 days of the onset of exacerbation, six had detectable levels of EP-P1, from 3.2 to 15.4 ng per milliliter. The concentration of EP-P1 was highest in individuals with more severe exacerbation in regard to extent and degree of impairment. The only person (patient 9) in this group who did not have an elevation of EP-P1 in CSF had increased quadriparesis coincident with a urinary tract infection and fever. The increased symptoms disappeared after the infection was controlled and in retrospect probably did not represent disease exacerbation.

Seven persons had recently had an exacerbation, but CSF was not obtained until 8 to 14 days after the clinical onset of the worsening. Although some of these exacerbations were severe, only one person had a level of 3.4 ng per milliliter. Owing to the known difficulties of dating the exact onset of a less severe exacerbation, as well as the possibilities of subtle or subclinical progression of disease, the establishment of an exact time of worsening may be imprecise. EP-P1 was not detected in the CSF in any of the 29 patients who were clinically stable or showed a gradually progressive course.

The changes in EP-P1 during the natural history of multiple sclerosis in a single patient cannot be determined without long-term studies over several years. However, data on four multiple sclerosis patients provide support for the relationship between multiple sclerosis disease activity and CSF EP-P1. In patient 1 (Table II) there was no detectable CSF EP-P1 15 days after onset of exacerbation, at a time when the patient was rapidly improving. In patient 4, CSF 4 weeks after the initial attack of multiple sclerosis and 3 months prior to the second episode showed no EP-P1. In a 36-year-old man who had had multiple sclerosis for 5 years, CSF obtained on three occasions during clinically stable periods over 18 months had no measurable EP-P1. A 28-year-old man with clinically stable multiple sclerosis had no detectable CSF EP-P1 on two occasions 14 months apart.

Many of the disease controls were disorders that may be confused with multiple sclerosis, showed CNS or peripheral nervous system demyelination pathologically, or were diseases that might alter the immune status. In this group, six patients had detectable levels above 2 ng per milliliter, the others were negative. (See Table IV). Four of the positive controls; (patients 15 through 18) had borderline levels of 2 to 2.4 ng of EP-P1 per milliliter of CSF on two or more separate determinations. Patient 15 was a 44-year-old man with serologically confirmed St. Louis encephalitis who made a full recovery. Patient 16 was a 51-year-old man with 2 years of gait ataxia who had mild cerebral cortical atrophy on pneumoencephalography. Patient 17 had a 3-hour transient ischemic attack involving the right cerebrum 5 days prior to lumber puncture. Patient 18 had a spastic paraparesis of middle-age onset and may have multiple sclerosis. Two patients who did not have multiple sclerosis had CSF EP-P1 levels of 11 and 20 ng per milliliter. Patient 19 had a cerebral infarction 2 weeks before CSF was removed. Patient 20 had diabetes mellitus, multi-infarct dementia, polyneuropathy, and diabetic glomerulopathy with nephrotic syndrome. He was in come due to metabolic disturbances of hyperglycemia and renal dysfunction when CSF was obtained.

shed into a body fluid and may provide a clinically useful laboratory test in the medical management of patients with this disorder.

The demonstration that myelin debris was present in the CSF sediment of two multiple sclerosis patients in acute phases prompted a number of studies attempting to quantify the well-characterized EP in CSF under similar conditions. Most of the assays previously used either failed to detect EP or reported EP in the CSF of many control patients who did not have multiple sclerosis. Based on the current findings, those results may have been due to differences in reactivities of the anti-EP, sensitivity of the assay system, the radiolabeled antigen used, or the timing of CSF collection.

One gel filtration radioimmunoassay was capable of measuring as little as 200 ng per milliliter and failed to Table IV Patients with diseases other than multiple sclerosis with detectable levels of encephalitogenic protein fragment P1 in cerebrospinal fluid

| | | | Cerebrospinal fluid | | | | | | |
|---|---|---|---|---|---|---|---|---|---|
| Number | Age, race sex | Diagnosis | Protein (mg/100 ml) | IgG (%) | Cells (per mm$^3$) | | Cells (% of WBC) | | EP-P1 ng/m |
| | | | | | RBC | WBC | PMN | Mono | |
| 15 | 44 BM | St. Louis encephalitis 8 days after onset | 59 | 10 | 0 | 78 | 2 | 98 | 2.0 |
| 16 | 51 BM | Gait ataxia and mild cerebral cortical atrophy | 37 | 9 | 23 | 1 | 0 | 100 | 2.3 |
| 17 | 55 WM | Diabetes mellitus, transient ischemic attack 5 days before | 85 | 11 | 0 | 1 | 0 | 100 | 2.0 |
| 18 | 57 BF | Progressive spastic paraparesis of 5 years' duration | 32 | 41 | 0 | 7 | 0 | 100 | 2.4 |
| 19 | 58 BM | Left cerebral infarction 14 days earlier | 60 | 11 | ND* | ND | ND | ND | 11.0 |
| 20 | 64 BM | Diabetes mellitus, nephrotic syndrome, dementia, neuropathy, metabolic coma | 125 | 14 | 0 | 0 | 0 | 0 | 20.0 |

Except for patient 18, the reasons for positive findings, especially in patients 19 and 20, were not apparent. Five other patients with encephalitis and four others with cerebral or brain stem infarction 2 to 20 days prior to lumbar puncture were negative.

Correlation of CSF EP-P1 with other CSF findings

The CSFs studied had protein concentrations of up to 380 mg per 100 ml and IgG percentages were as high as 41 percent. In the multiple sclerosis group, analyzed collectively or separately based on disease activity, there was no statistically significant correlation of the concentrations of EP-P1 with CSF total protein or IgG. In the controls, high levels of total CSF protein or IgG did not inhibit the antigen-antibody reaction in the radioimmunoassay. Xanthochromia and erythrocyte counts of up to 700 per cubic millimeter alone did not lead to a positive result, nor did previous Pantopaque myelography, performed on one individual 2 days before CSF was removed.

Histochemical, immunocytochemical, and electrophoretic investigations have demonstrated that EP is diminished or absent in areas of CNS demyelination in multiple sclerosis. Findings of the present study indicate that EP or, more likely, a fragment of EP containing, but not necessarily limited to, a portion of residues 43–88 appears in the CSF during acute phases of multiple sclerosis, presumably as a result of demyelination. These observations do not identify an initial or recurring cause of demyelination in multiple sclerosis, but they furnish evidence that a potential autoantigen is detect EP in CSF, some concentrated sevenfold by membrane ultrafiltration, from 16 persons with multiple sclerosis. There was no mention of disease activity in the multiple sclerosis patients. Since EP adheres readily to many surfaces, concentration of CSF by ultrafiltration prior to radioimmunoassay was avoided in the present study. An additional objection to concentration by ultrafiltration would be the loss of small but immunoreactive EP fragments not retained by the membrane. More extensive concentration of CSF 30- to 50-fold prior to gel filtration radioimmunoassay led to the detection of EP in CSF of a number of persons with multiple sclerosis and quantitatively less in some controls. A modification of this assay, based on interference of binding of $\alpha 2$-macroglobulin rather than anti-EP with $^{125}$I-EP, demonstrated higher levels of CSF EP in multiple sclerosis patients as well as in those who did not have the disease.

A radioimmunoassay that utilizes ethanol to separate bound from free $^{125}$I-EP and has a sensitivity to 6 ng per milliliter was reported to detect EP in CSF. Twelve of 20 CSF specimens, lyophilized and reconstituted to a 20-fold concentration, from multiple sclerosis patients contained material at a concentration of 10 ng per milliliter or higher interfering with the antibody-antigen reaction in the radioimmunoassay. As in the present investigation, there was a relationship between elevated CSF EP and disease activity, but one person with an acute transverse myelopathy and one with metachromatic leukodystrophy also had elevated levels. The identification of the antigenic regions recognized by the anti-EP, raised by immunization with spinal cord and rabbit EP, has not been reported.

The present study demonstrated that EP is released into the CSF during acute phases of multiple sclerosis, may exist in CSF in acute multiple sclerosis as a fragment of EP containing residues 43-88, appears to be cleared rapidly from the CSF, and is not correlated with either CSF total protein or IgG content. The pleocytosis noted in many of, but not restricted to, the acute-phase patients with CSF EP-P1 could suggest that the demyelination resulting in EP-P1 release into CSF was itself sufficient to provoke a pleocytosis or that the cells were a result of a chemotactic response to the released EP or its fragments. Effects on membranes of intact EP are well known. There are likely to be numerous mechanisms for pleocytosis, and patients with encephalitis and 300 to 400 leukocytes per cubic millimeter of CSF had no detectable CSF EP-P1.

Although CSF EP-P1 was found at similar levels in only six of 117 control patients without multiple sclerosis, the radioimmunoassay system utilized did not permit an absolute distinction between multiple sclerosis and other disorders. In only two of the six was the value clearly above the lower limits of detection and within the range of concentration noted in acute phases of multiple sclerosis. There was no apparently common feature in these two cases.

Whether the material in the CSF is the same as that in multiple sclerosis was not determined. In persons with multiple sclerosis, brain tumor or stroke, the appearance in CSF of material binding to polyriboguanylic acid has been reported. Although EP binds to DNA, a relationship between the polyriboguanylic acid-binding substances and EP is unknown. The extent of the molecular regions of EP present in CSF from positive controls and multiple sclerosis patients may be dissimilar, and there may be other differences such as temporal features of appearance and disappearance.

Several conditions sampled were unexpectedly negative. Demyelination can be extensive, although usually more chronic in course, in subacute sclerosing panencephalitis, but all four cases were without detectable CSF EP-P1. A protein chemically and immunochemically similar to EP exists in peripheral nervous system myelin, but there was no detectable EP-P1 during the acute phase in four persons with the Guillain-Barré syndrome, in which there is peripheral nervous system demyelination.

Most of the existing data on EP is derived from the study of bovine or other species' EPs. Throughout the present study human EP was used. EP isolated from multiple sclerosis brain was part of the immunogen, and nonmultiple sclerosis EP served as the source of antigen in the radioimmunoassay. The demonstration of EP fragments in CSF necessitated that EP-P1 rather than EP be the radioiodinated antigen in the radioimmunoassay. Large levels of EP-P1 went undetected in the radioimmunoassay when $^{125}$I-EP was the antigen. The use of $^{125}$I-EP-P1 as antigen made the detection of EP-P1 possible and increased the sensitivity of the radioimmunoassay in detecting EP. The increased sensitivity to EP raises the possibility that the $^{125}$I-EP-P1 also promoted a reaction with a population of high-affinity antibodies or presented a conformational alignment more similar to the EP or fragments thereof in CSF. The potential complexities in identification of the antigen reacting in radioimmunoassay have been exemplified in the immunochemical heterogeneity of parathormone in human serum.

The mechanisms responsible for the appearance of EP-P1 could be important in understanding normal metabolism and degradation of EP. The presence of acid proteinase in multiple sclerosis lesions could lead to the release of EP-P1. However, information presently available does not distinguish between the possibilities of EP degradation by an enzyme within brain or only after release into CSF. The region of EP spanning residues 43-88 is relatively resistant to in vitro and in situ proteolysis by pepsin or pepsinlike enzymes. This feature may account for the appearance of EP-P1 in CSF. It is not known if the appearance of this fragment in multiple sclerosis but not subacute sclerosing panencephalitis, encephalitis, and numerous other controls is a result of increased susceptibility of EP in persons with multiple sclerosis to breakdown or of the generation of unusual EP fragments in multiple sclerosis patients that can be less readily absorbed from CSF or further degraded. Characterization of the EP fragments appearing in CSF of multiple sclerosis patients and others is currently under investigation.

The appearance of EP or its fragments raises the possibility that sensitization of this normally sequestered immunogen might be involved in the perpetuation of the disease process in multiple sclerosis. Although efforts to find anti-EP antibodies in serum and CSF of multiple sclerosis patients have nearly always been negative and studies of cell-mediated immunity to EP in multiple sclerosis inconclusive, it has been demonstrated that human lymphocytes bear receptors for EP.

At present, quantifying CSF EP-P1 appears to be a substantial improvement over any test heretofore available for assessing disease activity in multiple sclerosis.

The materials employed as described above included: CM-cellulose(CM-52) and DEAE-cellulose(DE-52) manufactured by Reeve Angel, Clifton, N.J.; Sephadex manufactured by Pharmacia Fine Chemicals, Inc., Piscataway, N.J.; Bio-Gel P-2 (100 to 200 mesh), manufactured by Bio-Rad Laboratories, Richmond, Calif.; swine gastric mucosal pepsin (twice crystallized) manufactured by Worthington Biochemical Corp., Freehold, N.J.; crystalline rabbit serum albumin (RSA) and bovine serum albumin (BSA) manufactured by Miles Laboratories, Inc., Elkhart, Indiana; Methylated BSA (MBSA) and thymic histone manufactured by Sigma Chemical Co., St. Louis, Mo.; incomplete and complete Freund's adjuvants manufactured by Difco Laboratories, Detroit, Michigan; chloramine T manufactured by Eastman Kodak Co., Rochester, N.Y.; carrier-free iodine 125 ($^{125}$I) manufactured by Amersham-Searle, Chicago, Ill,; lactoperoxidase manufactured by Calibiochem, La Jolla, Calif;, and polypropylene test tubes, Number 2053 manufactured by Falcon, Oxnard, Calif.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. In a method for detecting an acute phase of multiple sclerosis in a patient, the improvement which comprises subjecting the cerebrospinal fluid of said patient to a double antibody radioimmunoassay procedure to determine the presence therein of a fragment of encephalitogenic protein (EP) containing residues 43–88, said fragment being designated EP-P1, said radioimmunoassay procedure comprising forming a radioimmunoassay reaction mixture containing said cerebrospinal fluid, rabbit anti-EP serum, and $^{125}$I-EP-P1 to produce a radioactive product including the reaction product of said anti-EP serum and said $^{125}$I-EP-P1, adding a second antibody to precipitate said radioactive product, and measuring the radioactivity of said precipitated radioactive product from which the presence of the EP-P1 fragment is determined.

2. The method of claim 1 wherein said radioimmunoassay reaction mixture also contains tris-acetate buffer and methylated bovine serum albumin.

3. The method of claim 1 wherein the second antibody is goat anti-rabbit IgG.

* * * * *